United States Patent [19]

Suzuki et al.

[11] Patent Number: 4,524,622

[45] Date of Patent: Jun. 25, 1985

[54] METHOD AND APPARATUS OF ULTRASONIC FLAW DETECTION

[75] Inventors: Norio Suzuki; Hiroshi Kajikawa, both of Kobe; Tadashi Nishikawa, Osaka, all of Japan

[73] Assignee: Kabushiki Kaisha Kobe Seiko Sho, Kobe, Japan

[21] Appl. No.: 514,864

[22] Filed: Jul. 18, 1983

[30] Foreign Application Priority Data

| Jul. 20, 1982 [JP] | Japan | 57-127184 |
| Jul. 20, 1982 [JP] | Japan | 57-127183 |
| Jul. 20, 1982 [JP] | Japan | 57-127185 |
| Jul. 20, 1982 [JP] | Japan | 57-127186 |

[51] Int. Cl.$^3$ .................................. G01N 29/04
[52] U.S. Cl. ........................... 73/620; 73/625; 73/628; 73/640
[58] Field of Search .............. 73/625, 626, 618, 628, 73/620, 637, 640

[56] References Cited

U.S. PATENT DOCUMENTS

| 3,280,621 | 10/1966 | Cardinal et al. |  |
| 3,977,236 | 8/1976 | Raatz et al. |  |
| 4,402,223 | 9/1983 | Naumann, Jr. et al. | 73/625 |
| 4,413,521 | 11/1983 | Van Kemenade | 73/626 |

FOREIGN PATENT DOCUMENTS

| 57-013352 | 1/1982 | Japan . |  |
| 1453065 | 10/1976 | United Kingdom . |  |
| 406156 | 4/1974 | U.S.S.R. | 73/626 |

OTHER PUBLICATIONS

Article, "Ultrasonic Data Analysis Using a Computer" by R. D. Sachs, J. D. Elkins & J. H. Smith, Oak Ridge, Tennessee.
Soviet Journal of Nondestructive Testing, vol. 16, No. 3, 1980, New York, A. K. Gurvich et al., "Statement of the Problem of Working Out Algorithms for Identifying Flaws in Welded Joints on the Basis of Data of Ultrasonic Quality Control", pp. 151-158.

*Primary Examiner*—Howard A. Birmiel
*Attorney, Agent, or Firm*—Oblon, Fisher, Spivak, McClelland & Maier

[57] ABSTRACT

A method and an apparatus of ultrasonic flaw detection suitable for detecting internal cavern defects of a material, the method involving the mounting on a rotary body of a plural number of skew probes in equidistant positions in the circumferential direction of the rotary body to provide a corresponding number of channels for transmitting and receiving ultrasonic beams in a direction intersecting the axis of rotation of the rotary body at different depths in an inspection zone of a material positioned oppositely to the probes. The rotary body is turned to revolve the probes through 360° about the axis of rotation while transmitting and receiving the ultrasonic pulses. Selected flaw patterns are produced from the peak values of the echoes received at the detection gates of the respective channels in relation with the direction of incidence of the ultrasonic beams. The direction, inclination, size and depth of a detected defect is deciphered by correlation processing of the detected flaw patterns with a number of predetermined reference patterns in order to provide for judging the harmfulness of the detected defect.

8 Claims, 28 Drawing Figures

FIGURE 15
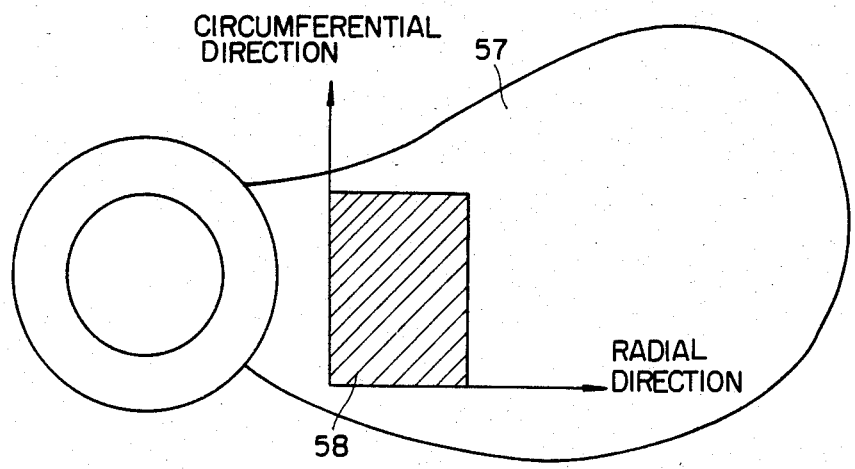
FIGURE 16(A)
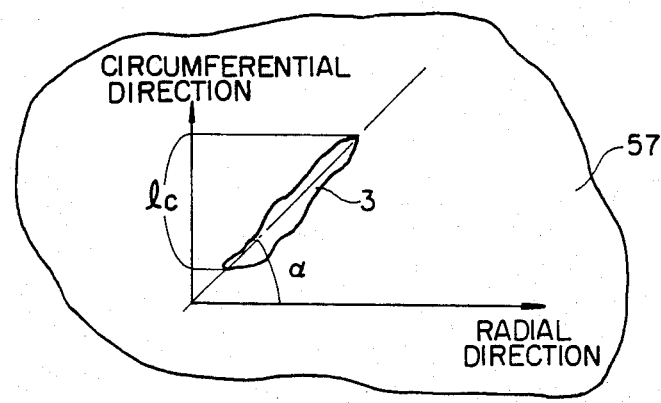
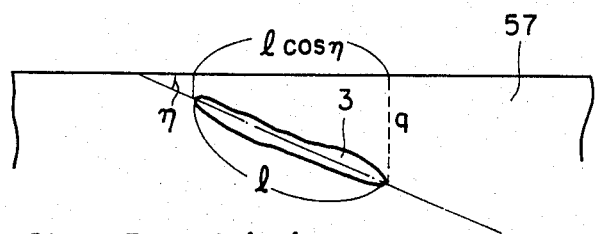
FIGURE 16(B)

METHOD AND APPARATUS OF ULTRASONIC FLAW DETECTION

BACKGROUND OF THE INVENTION

1. Field of the Invention

This invention relates to a method and apparatus of ultrasonic flaw detection, and more particularly to a method and apparatus capable of high-speed judging of the harm caused by defects which includes detecting the directions, inclinations, sizes and depths of cavern voids or other internal flaws of various materials.

2. Description of the Prior Art

Cast stocks sometimes contain oblique cavern voids due to a spout of gases which take place in the casting stage. In this connection, few attempts have ever been made to analyze the shape of an internal defect in terms of determining its harmfulness to the strength of a material intended for a specific use, except simple definitions of harmfulness by the dimensions of a defect as projected on the surface. However, in view of the particular directionality of the stress to be applied on the material, the harmfulness of a cavern void of a given size normally varies depending upon whether it extends in X-direction or Y-direction. From the standpoint of the strength of a material, the allowable defect size in X-direction of a material differs from that of Y-direction. Under these circumstances, it is a matter of utmost importance to detect the shaped (directions, inclinations and sizes) of internal cavern defects with accuracy.

For the detection of internal defects as mentioned above, the so-called ultrasonic methods have been utilized in which an ultrasonic pulse is transmitted into a material to receive the echoes from the internal defects. However, the conventional ultrasonic methods in which the ultrasonic pulses are transmitted and received through a single probe or a plural number of probes which are scanned along the surface in predetermined directions in an inspection zone of a material, can display only the position and roughly estimated size of the defects which are calculated from very limited information such as the propagation time and direction of the refraction angle and the amplitude of the ultrasonic pulse on a display medium and therefore the conventional ultrasonic methods can hardly determine the shapes (directions, inclinations and sizes) of the crosswise (inclined) cavern defects.

In order to solve this problems, the present inventors developed a method which employs a revolving inclined probe to transmit and receive the ultrasonic pulse in a direction intersecting a rotational axis in an inspection zone of a material under inspection. The probe is turned through 360° about the rotational axis while transmitting and receiving ultrasonic pulses, and indicating the peak values of echoes received at the flaw detection gate as a detected flaw pattern on a display medium for judging therefrom the direction, inclination, size and depth of the detected defect. This method has a great advantage over the above-mentioned conventional methods in that it is capable of accurately determining the shapes of internal defects such as the directions, inclinations and sizes thereof. However, the inventor' prior method has a drawback in that it takes a long time to detect the depth of a defect by a single probe, since the same operation has to be repeated a number of times, varying the depth of inspection each time. Further, the above-mentioned methods all rely on the operator with regard to the judgement of the harmfulness of a detected defect, which is relatively easy in the flaw detection of a small piece of material but difficult to adopt in the on-line flaw detection of large materials.

SUMMARY OF THE INVENTION

It is an object of the present invention to provide ultrasonic a flaw detection method and apparatus which will overcome the above-mentioned difficulties or problems of the conventional methods.

It is a more particular object of the present invention to provide a method and an apparatus of ultrasonic detection which employs a plural number of inclined probe members supported on a rotary body to provide a plural number of channels for transmitting and receiving ultrasonic pulses having different depths of inspection.

It is another object of the present invention to provide a method and an apparatus of ultrasonic flaw detection which employs advice for producing detected flaw patterns from the peak values of echoes received at the gates of the respective channels and correlating the detected flaw patterns with a number of predetermined reference patterns to judge the harmfulness of the defect.

It is a further object of the present invention to provide a method and an apparatus of ultrasonic flaw detection of the sort mentioned above, employs a computer or digital logic circuits for automatically providing a judgement as to the harmfulness of a detected defect on the basis of the results of the correlation processing of the detected flaw patterns.

According to a fundamental aspect of the present invention, there is provided an ultrasonic flaw detection method particularly suitable for detecting internal cavern defects of a material. The method involves: mounting on a rotary body a plural number of inclined probes in equidistant positions in the circumferential direction of the rotary body to provide a corresponding number of channels for transmitting and receiving ultrasonic pulses in a direction intersecting the axis of rotation of the rotary body at different depths in an inspection zone of a material positioned opposite to the probes. The rotary body is then turned to revolve the skew probes through 360° about the axis of rotation while transmitting and receiving the ultrasonic pulses. Detected flaw patterns are then produced from the peak values of the echoes received at the detection gates of the respective channels in relation with the direction of incidence of the ultrasonic pulses. Finally the direction, inclination, size and depth of a detected defect is deciphered from correlation processing of the detected flaw patterns with a number of predetermined reference patterns for judging the harmfulness of the detected defect.

According to the present invention, there is also provided an apparatus for carrying out the above-described method, which includes: a plural number of inclined probes mounted on a rotary body in equidistant positions in the circumferential direction of the rotary body for providing a plural number of channels for transmitting and receiving the ultrasonic pulses in a direction intersecting the axis of rotation of the rotary body at different depths in an inspection zone of a material positioned opposingly to the inclined probes. A a rotational drive mechanism turns the rotary body to revolve the skew probes through 360° about the axis of rotation while transmitting and receiving the ultrasonic pulses peak-hold and memory circuit is provided for each one of the detection channels for producing and storing a plural number of detected flaw patterns in relation with the directions of incidence of the ultrasonic pulses, from the peak values of echoes received at the direction gates of the respective channels. A correlator deciphers the direction, inclination, size and depth of the detected defect by correlation processing of the detected flaw patterns with a number of predetermined reference patterns.

The above and other objects, features and advantages of the present invention will become apparent from the following description and appended claims, taken in conjunction with the accompanying drawings which show by way of example some illustrative embodiments of the invention.

BRIEF DESCRIPTION OF THE DRAWINGS

In the accompanying drawings:

FIG. 15 is a fragmentary plan view of a propeller;

FIGS. 16(A) and 16(B) are diagrammatic illustrations explanatory of a harmful defect;

DETAILED DESCRIPTION OF THE PREFERRED EMBODIMENTS

Figure 1A:
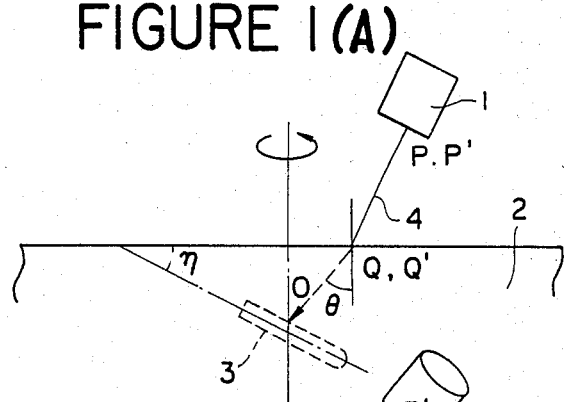
FIGS. 1(A) and 1(B) are diagrammatic illustrations showing the path of an ultrasonic pulse.
Figure 1B:
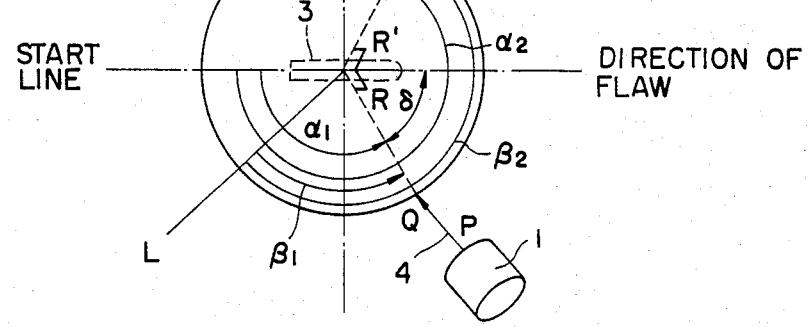

The principles of the present invention are explained with reference to FIGS. 1(A) and 1(B) which show the path of an ultrasonic pulse 4 in a angled beam ultrasonic flaw detector using a probe 1, the beam having a refraction angle of $\theta$ for detecting a cavern void 3 which exists in a material 2 with an angle of inclination $\eta(\theta \geq \eta)$. As seen in FIGS. 1(A) and 1(B), when the probe 1 is turned to make one revolution in the arrowed direction about the axis of rotation from the start line position (i.e., the position in the longitudinal direction of the defect as projected on the surface of the material) while transmitting an ultrasonic pulse 4, the direction of the incident ultrasonic pulse becomes perpendicular to the defect 3 at two different positions, namely, at the positions distant from the start line by rotational angles $\alpha_1$ and $\alpha_2 (\alpha_2 > \alpha_1)$. At these positions, the ultrasonic pulse takes the paths of P→Q→R→Q→P and P'→Q'→R'→Q'→R' in FIG. 1. Therefore, it is known from simple geometric calculations that the angles $\alpha$, $\eta$ and $\theta$ are in the relationship expressed by the following Equation (1).

$$\cos\left(\frac{\alpha_2 - \alpha_1}{2}\right) = \frac{\tan \eta}{\tan \theta} \quad (1)$$

Figure 2:
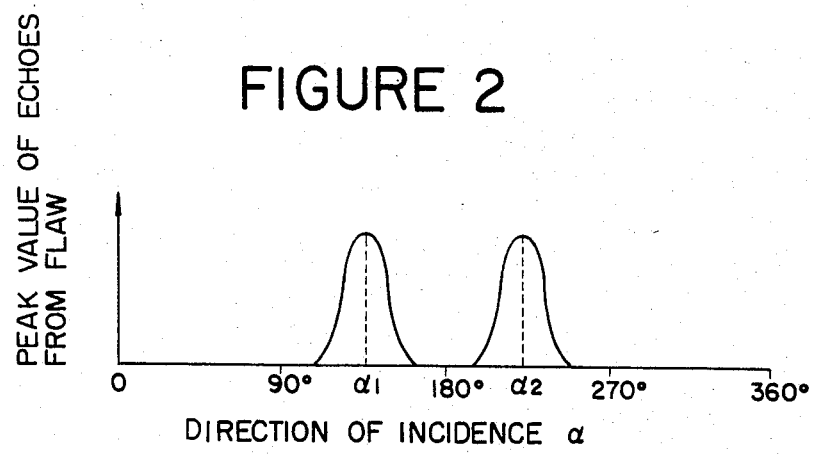
FIG. 2 is a waveform diagram of a detected flaw pattern.

FIG. 2 shows a detected flaw pattern obtained by plotting against the direction of incidence $\alpha$ the peak values of the ultrasonic echoes 4 which was actually transmitted and received sequentially along the locus C of the points of incidence shown in FIG. 1(B) while revolving the probe 1. The angular characteristics of this sort of detached flaw pattern are defined by the Equation (1), and the maximum peak value depends on the size of the defect 3. In order to know the relationship between the size of the defect 3 and the height of the echoes, it is possible to resort either to the Distance-Amplitude Curves used in the conventional flaw detection or to actually measured values of artificial flaws. It will be therefore understood that the flaw detection pattern of FIG. 2 contains the data with regard to the direction, inclination and size of the defect 3.

The direction of the start line is selected such that it coincides with a particular direction related to the shape of the material 2 to be inspected, for example, the longitudinal direction of the material 2, measuring the direction of the defect 3 from that start line. In this instance, the direction of the defect 3 is expressed by the following formulas.

$$\frac{\beta_1 + \beta_2}{2} \quad (\beta_2 - \beta_1 \leq 180°) \quad (2)$$

$$\frac{\beta_1 + \beta_2}{2} + 180° (\beta_2 - \beta_1 \geq 180°) \quad (3)$$

and the inclination of $\eta$ of the defect 3 is expressed by the following equations.

$$\cos\left(\frac{\beta_2 - \beta_1}{2}\right) = \frac{\tan \eta}{\tan \theta} \quad (\beta_2 - \beta_1 \leq 180°) \quad (4)$$

-continued $$\cos\left(180° - \frac{\beta_2 - \beta_1}{2}\right) = \frac{\tan \eta}{\tan \theta} \quad (\beta_2 - \beta_1 \geqq 180°) \quad (5)$$

On the other hand, from a practical standpoint, it suffices if the detection of the inclination $\eta$ of the defect 3 is feasible in the range of 0°–45° with an error of ±2.5°. Therefore, the present invention adopted the correlation method to let the flaw detector make the foregoing judgements automatically by a correlation processing circuit.

The correlation processing is expressed by the following equation.

$$C(S) = \frac{1}{360} \int_0^{360} r(\alpha) f(\alpha + S) d\alpha \quad (6)$$

in which $f(\alpha)$ and $r(\alpha)$ are arbitrary functions defined by $0 \leqq \alpha \leqq 360$. The correlation processing which is recently applied to the pattern recognition in image processing technology and the error corrections in communication technology is used in the present invention to compare detected flaw patterns of an unknown defect with a number of reference patterns, judging the flaw pattern as being similar to one of the reference patterns with the closest similarity.

Figure 3:
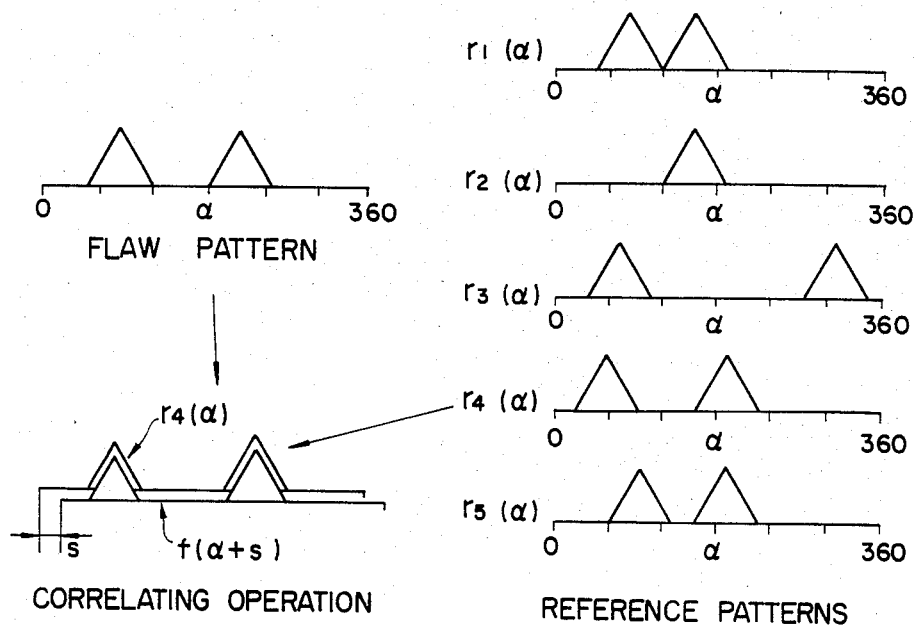
FIG. 3 is a diagrammatic illustration explanatory of the correlation processing.

Now, the operation of the correlation processing is explained briefly with reference to FIG. 3 which shows by way of example a single detected flaw pattern and five kinds of reference patterns $r_1(\alpha)$ to $r_5(\alpha)$. In the instance of one of ordinary skill in the art of pattern recognition, one would compare the detected flaw pattern with the reference patterns as to the number of peaks, the peak-to-peak distance and the angles of slopes. Then, one would check the degree of similarity to each reference pattern and make a decision that the detected flaw pattern is identical to the pattern $r_4(\alpha)$ in consideration of the close conformity therewith. This operation is called correlation processing and, in order to check the conformity quantitatively, Equation (6) is introduced for determining the value which is proportional to the sum of the products of the overlapping portions. The symbol S in Equation (6) indicates the amount of deviation between the two patterns in the direction of the horizontal axis when superimposed for comparison as mentioned hereinbefore.

In this instance, the reference patterns are prepared on the basis of actually measured values of artificial cylindrical drilled holes or by calculations according to Equation (1). Since the characteristics (directions, inclinations etc.) of the artificial cylindrical drilled holes are known, the amount of deviation S gives the discrepancy between the direction of a cylindrical drilled hole and a detected defect.

Figure 4:
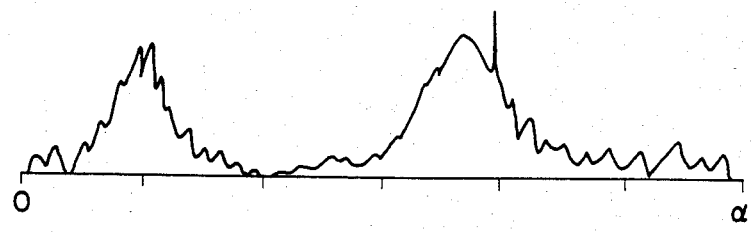
FIG. 4 is a waveform diagram of an actually detected flaw pattern.

In the application of the above-described principles, a number of reference patterns are prepared, for example, from 10 kinds of cylindrical drilled holes which are same in the direction, length and depth of the reflecting surface but which have different angles of inclination of 0, 5, 10, 15, 20, 25, 30, 35, 40 and 45 degrees, respectively, and an obtained flaw detection pattern is correlated with the respective reference patterns for the detection of the direction and inclination of the defect. In this instance, the defect can be classified in a facilitated manner if the maximum values of the reference patterns are set at a predetermined level. The correlation method which is often used for the improvement of S/N ratio in signal processing can also be effectively applied to those cases where the detected flaw pattern contains noises as shown in FIG. 4. In actual operations, the detected flaw patterns contain such noises in most cases, so that it becomes extremely difficult for the machines to measure the number of peaks and the pek-to-peak distances correctly.

Figure 5:
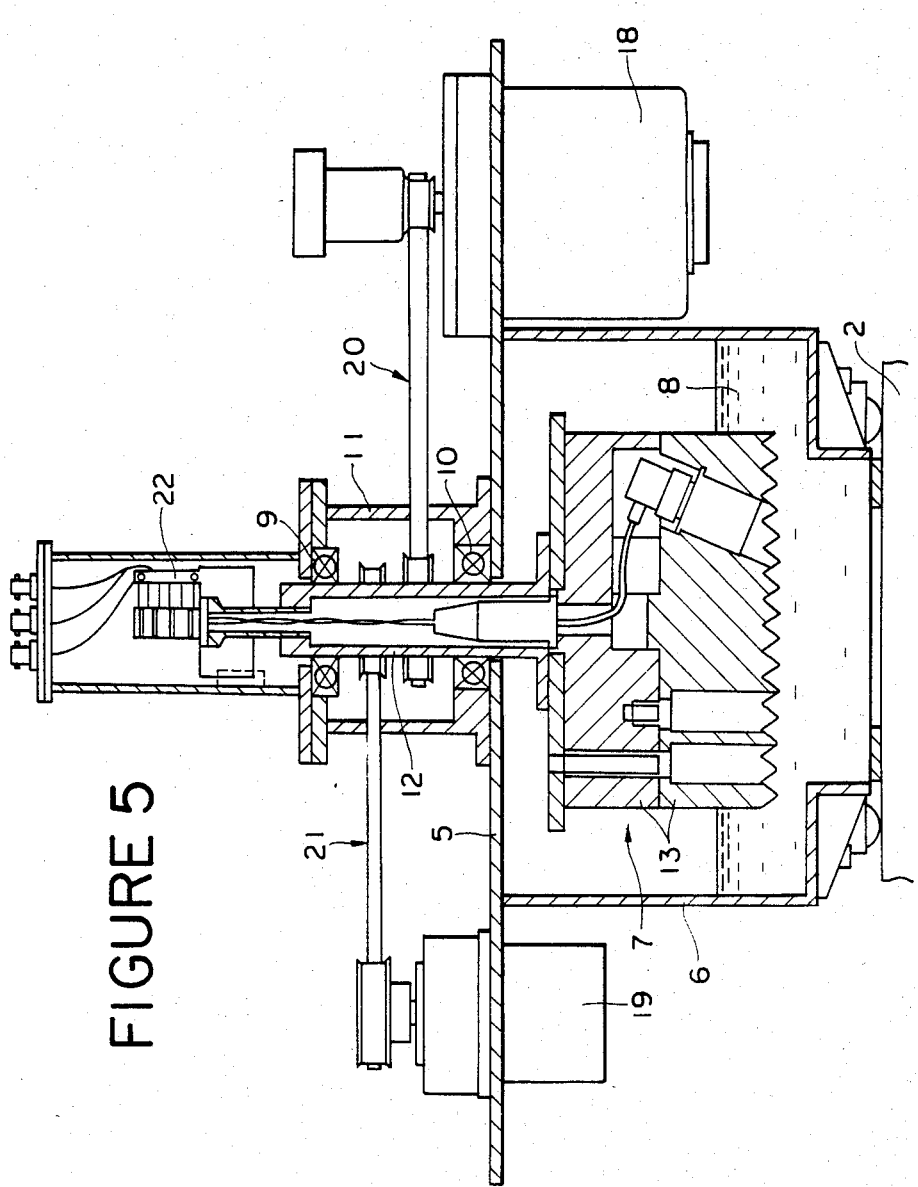
FIG. 5 is a sectional view of a probe rotating mechanism.
Figure 6:
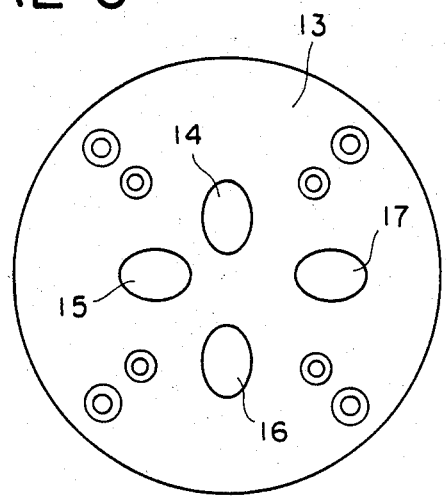
FIG. 6 is a bottom view of a probe holder.

Referring now to FIGS. 5 and 6, there is illustrated an apparatus for carrying out the flaw detection method of the present invention, employing four probes. In these figures, designated at 5 is a support plate which is movable in the directions of X- and Y-axes for scanning purposes, and supports on its underside a water tank 6 which is movable along a material 2 to be inspected. The water tank 6 accommodates a probe rotating mechanism 7 and contains water 8 therein. The probe rotating mechanism 7 includes a cylindrical rotational shaft 12 which is rotatably supported in a bearing case 11 on the support plate 5 through bearings 9 and 10, and a probe holder 13 which is mounted at the lower end of the rotational shaft 12 and has four inclined probes 14 and 17 built thereinto at the intervals of 90° in the circumferential direction. The probes 14 to 17 are adapted to inspect the range of 20 mm from the surface of the material 2 at a scanning pitch of 8 mm in this particular example although they are not limited to any specific range or scanning pitch of inspection. The respective probes 14 to 17 are arranged to transmit ultrasonic pulses 14a to 17a with a refraction angle $\theta$ of 45° and a diameter of 9.2 mm and are located at different positions from the axis of rotation so that the ultrasonic beams 14a to 17a intersect the axis of rotation at the depths of 2.5 mm, 7.5 mm, 12.5 mm and 17.5 mm, respectively. Therefore, the defects in the inspection zone, more specifically, in the diamond-like areas (the hatched areas) of FIG. 7 can be detected by receiving the echoes at the respective detection gates 14b to 17b during one revolution of the probes 14 to 17. In FIG. 5, indicated at 18 is a motor for driving the probe rotating mechanism 7, and at 19 a rotary encoder which is mounted on the support plate 5 for detecting the rotational angle of the probe rotating mechanism 7, respectively rotationally coupled with the rotational shaft 12 through belt drive mechanisms 20 and 21. The reference numeral 22 denotes a slip ring for transmitting and receiving ultrasonic signals to and from the respective probes 14 to 17 on the probe rotating mechanism 7.

The operation of flaw detection is hereafter described with reference to the block diagram of the signal processor shown in FIG. 8. Indicated at 23 is a scan mechanism for scanning the probe rotating mechanism 7 in the directions of X- and Y-axes, and at 24 a controller which controls the scan mechanism 23. The signal processor includes pulser receivers provided respectively for the four channels $CH_1$ to $CH_4$ of the probes 14 to 17 and analog peak holding circuits 29 to 32. In a flaw detecting operation, ultrasonic pulses 14a to 17a are transmitted into the material 2 from the probes 14 to 17 which is rotated by the probe rotating mechanism 7, and the pulser receivers 25 to 28 through the probes 14 to 17, respectively, detecting the analog peak holding circuits 29 to 32 the peak values of the signal appearing at the flaw detection gates 14b to 17 b. Denoted at 33 to 36 are A/D converters for converting the peak values into digital signals, and at 37 to 40 shift registers which temporarily store the peak values at every (360/128)° or in 128 directions of incidence, which constitute flaw detection patterns. The direction of incidence is detected by the rotary encoder 19 and, needless to say, a detected flaw pattern is obtained from each channel in relation with the detection of the direction of incidence. Indicated at 42 is a data selector, and at 43 a digital correlator which performs the correlation processing of detected flaw patterns of the respective channels sequentially fed thereto through the data selector 42, with the reference patterns stored in a memory 41. The maximum values of the correlation of the respective channels are detected by a digital peak detector 44, while simultaneously the amounts of deviation S are detected by a data latch 45. The maximum correlation values Cmi (i=1, 2, 3, 4,), the amounts of deviation Si (i=1, 2, 3, 4,) and the current position (x, y) and the scan mechanism 23 which are detected in this manner are put in a predetermined order and sorted in the shift register 47. The signal processing after the digital correlator 43 can be carried out by a software by the use of a computer as will be described hereinafter although it takes a long time in such a case.

Figure 9:
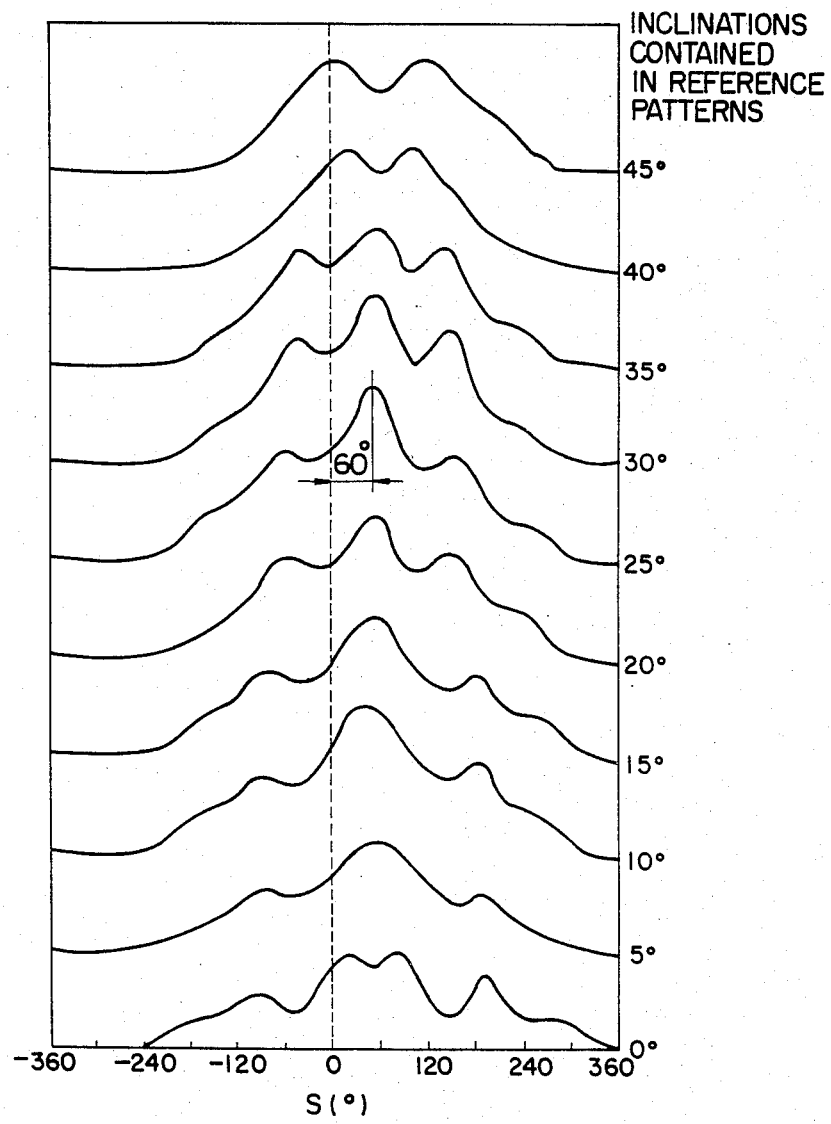
FIG. 9 is a diagram of waveforms obtained after D/A conversion of the output signals of the digital correlator of FIG. 8.
Figure 11A:
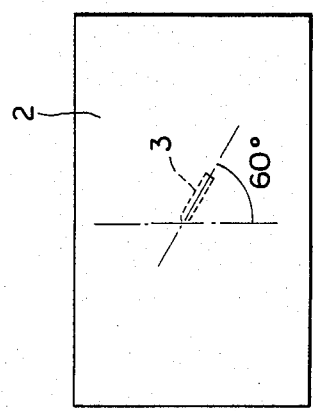
FIGS. 11(A) and 11(B) are diagrammatic illustrations of the same defect.
Figure 11B:
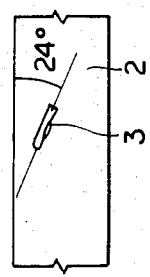
Figure 10:
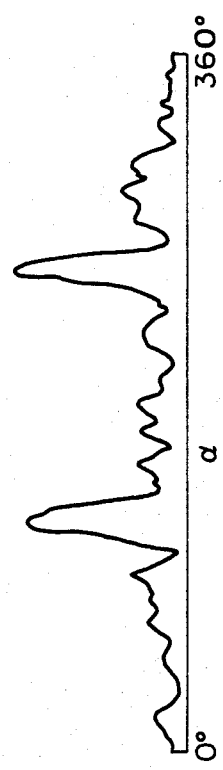
FIG. 10 is a waveform diagram of a detected flaw pattern obtained from a defect with an inclination of $\eta = 24°$.

The output of the digital correlator 43 after D/A conversion is shown in FIG. 9, and the corresponding detected flaw pattern is shown in FIG. 10. The condition of the defect 3 itself is shown in FIGS. 11(A) and 11(B). The inclination $\eta$ of the defect 3 is 24°, and it is seen from FIG. 9 that it has the closest correlation with the reference pattern of 25°. It is also known from the +60° deviation of the peak value of correlation from the center (=0°) that the direction of the defect 3 is at the angle of 60° with a particular direction of the material 2.

These judgements are made easily and at a high speed in an actual operation by transferring the data of the shift register 47 to the computer (not shown) through an interface 48. The data which are transferred to the computer are processed in the following manner.

Figure 7:
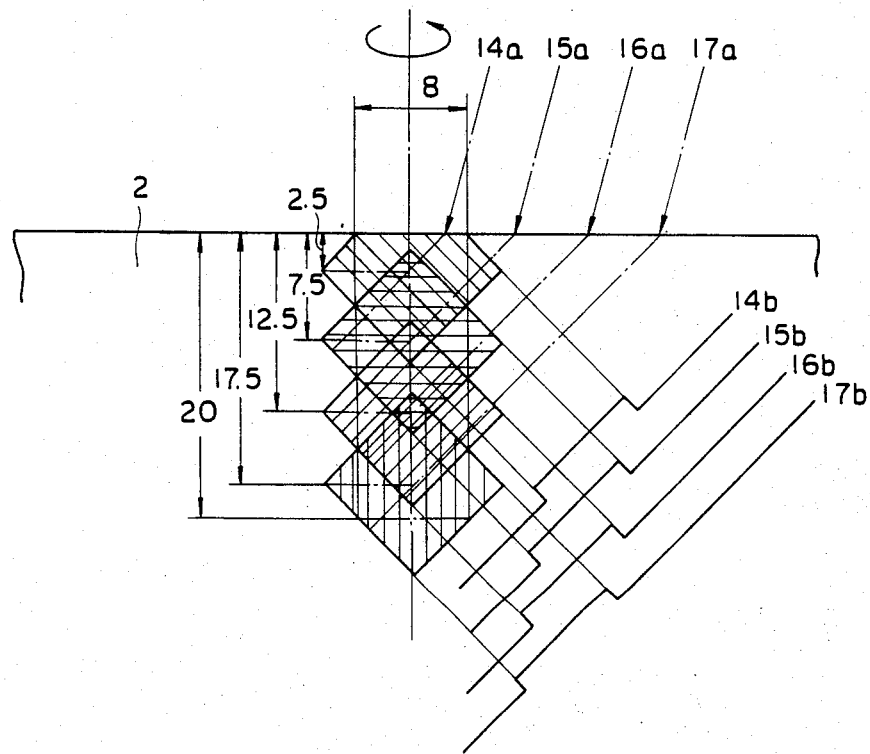
FIG. 7 is a diagrammatic illustration of the inspection zone.

As shown in FIG. 7, the ultrasonic pulses 14a to 17a of the respective channels are overlapped one another within the inspecting materal 2, so that significant correlation values appear in a plural number of channels with regard to a single defect 3. Therefore, in such a case, the depth of the reflecting surface of the defect 3 is calculated according to the following equation.

$$d = \frac{\sum_{i=1}^{4} Cmi \cdot di}{\sum_{i=1}^{4} Cmi} \quad (7)$$

Figure 12:
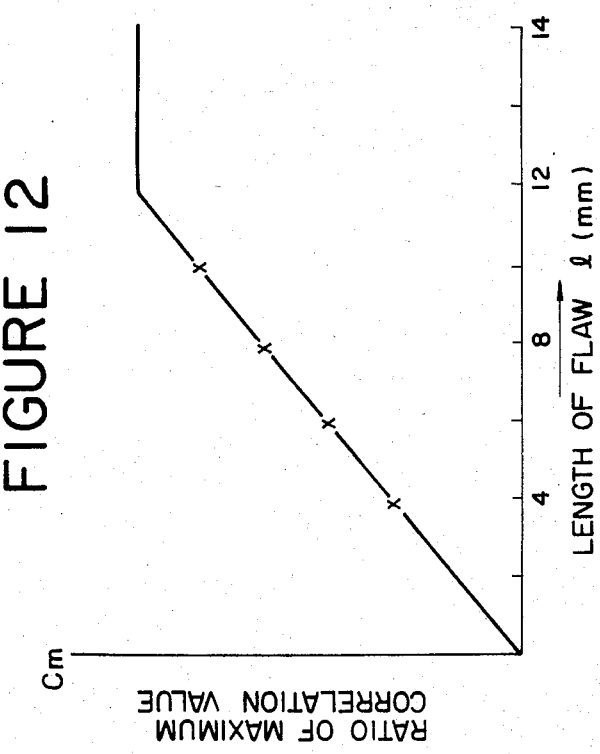
FIG. 12 is a diagram of the defect length vs. the ratio of the maximum correlation value.

Then, the deviation of the reflecting surface of the defect 3 from the central axis of the ultrasonic beam is correlated according to the following equation.

$$Cmi' = \frac{Cmi}{1 - k|d - di|} \quad (8)$$

in which k is a proportional constant depending upon the probe. The length of the defect 3 is judged from the value of Cmi' thus obtained. FIG. 12 shows the maximum correlation values (marked with "X") between a defect with a diameter of $\phi2$, a length of l and an inclination of 35° and a reference pattern with an inclination $\eta=35°$. It is possible to calculate from these data the effects of deviations of the reflecting surface of the central axis of the ultrasonic beam on the correlation value, for determining the value of k.

During the flaw detecting operation, the signals of the X-Y position of the probe rotating mechanism 7 (corresponding to the position of the defect) are fed from the controller 24 through the data selector 46 for storage in the shift register 47 and transferred to the computer through the interface 48 along with the data of the maximum correlation values and the like. These data are indicated on a graphic display as positional information of the defect 3 when the data of s harmful defect are displayed as an estimated figure of the flaw thereon afterwards. In FIG. 8, the reference numeral 49 denotes a timing controller. If desired, the probe rotating mechanism 7 may be replaced by an electronic scan type probes, but they are too expensive for the factory use at the present stage.

Figure 8:
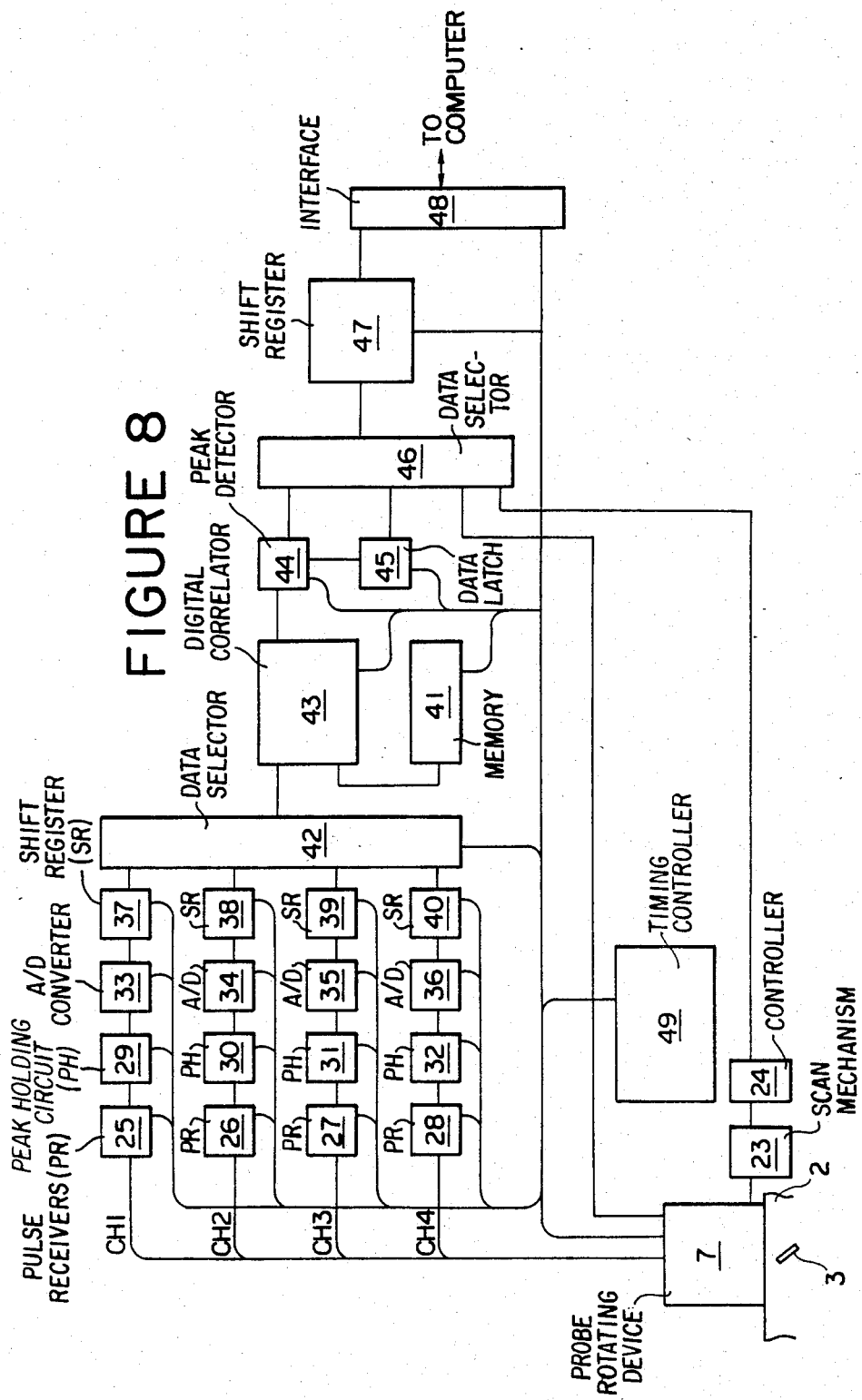
FIG. 8 is a block diagram of the flaw detection according to the invention.
Figure 13:
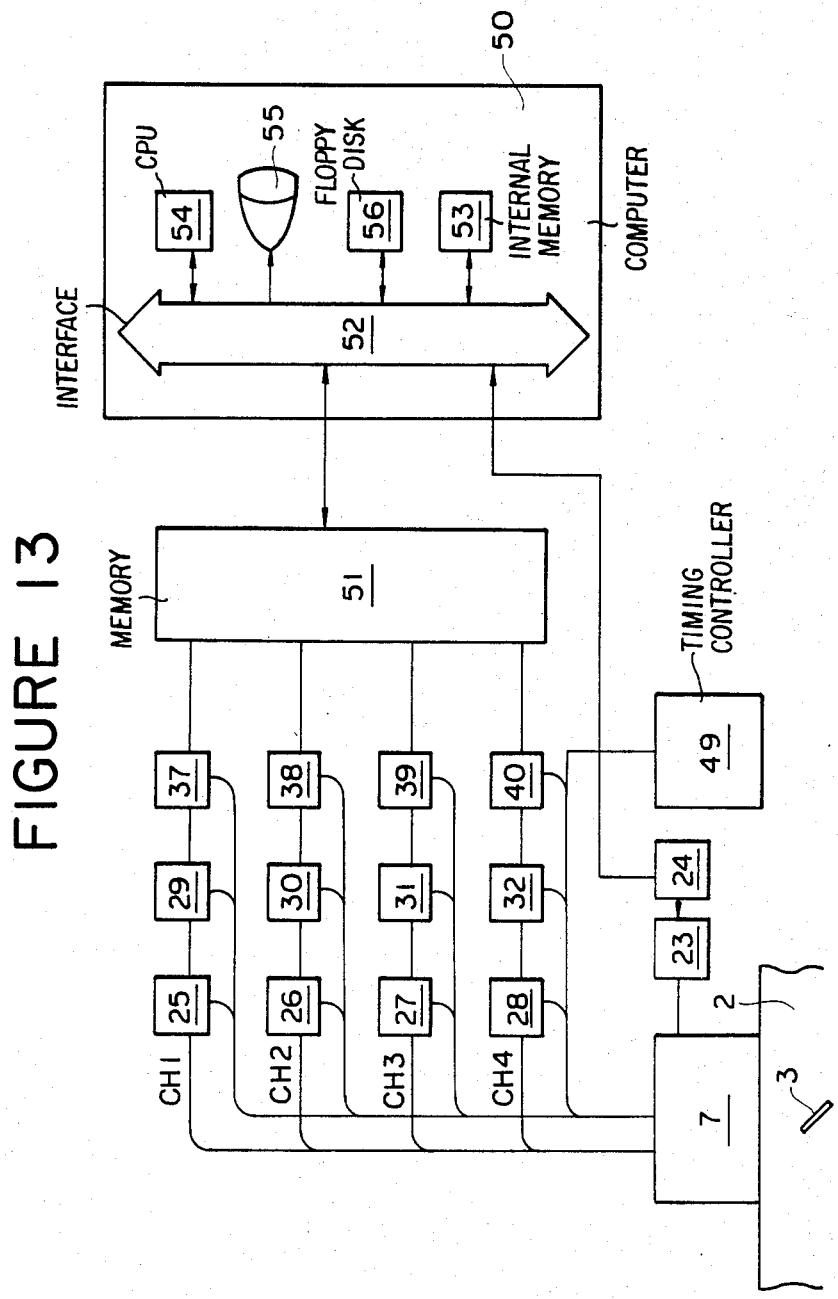
FIG. 13 is a block diagram.

Reference is no had to the block diagram of FIG. 13 which shows the processing flow on a software of the computer 50 during recognition of the shape of the defect 3, in which the components common to FIG. 8 are designated by similar reference numerals and their explanations are omitted to avoid repetitions. In this case, the peak values of echoes which are obtained during one revolution through the pulser receivers 25 to 28, analog peak holding circuits 29 to 32 and A/D converters 33 to 36 according to the rotational angles of the probes 14 to 17 are collected and stored in the memory 51 to form the detected flaw patterns. The memory 51 serves as an external memory of the computer 50, and the detected flaw pattern in the memory 51 is transferred by DMA to an internal memory 53 through an interface 52 for the computer 50 before the probes 14 to 17 start the first receive of ultrasonic pulses of the next recognition. The computer 50 includes a CPU 54, a CRT 55 for displaying the detected flaw data, and a floppy disk 56 for storing the flaw data.

Figure 14:
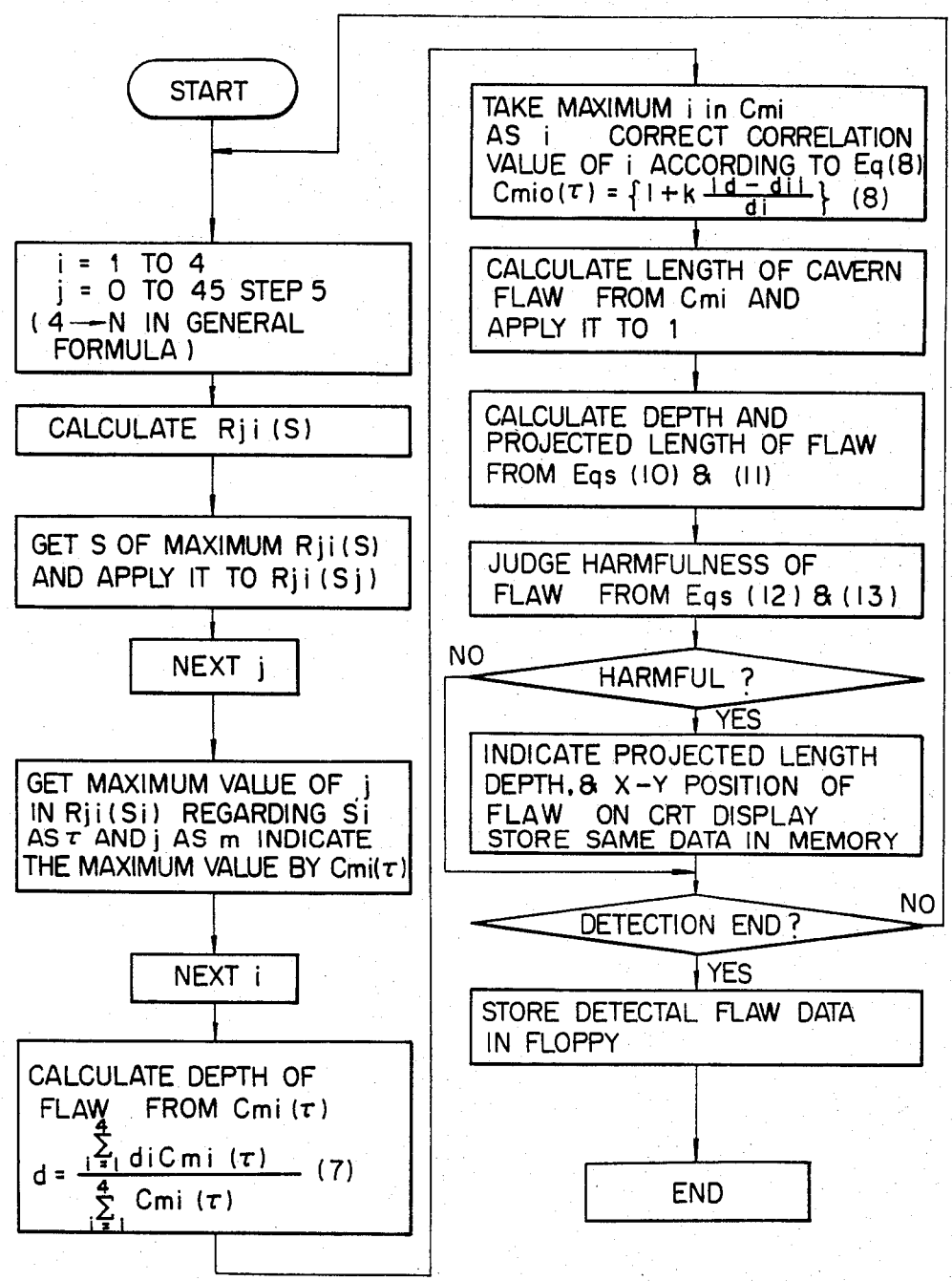
FIG. 14 is a flowchart of flaw detection.

The computer processes the signals according to the steps shown in the flowchart of FIG. 14, in which the detected flaw pattern is indicated by $Ai(\alpha)$. The subscripts "i" and "$\alpha$" indicate the channel and the rotational angle, respectively. The reference patterns are indicated by $Rj(\alpha)$ in which the subscript "$\gamma$" is the inclination of the defect. The correlation between $Ai(\alpha)$ and $Rj(\alpha)$ is expressed by the following equation.

$$Rji(S) = \frac{1}{360} \int_0^{360} Ai(\alpha)Rj(\alpha + S)d\alpha \quad (9)$$

The equation (9) is generally available in the form of a software package.

Figure 17:
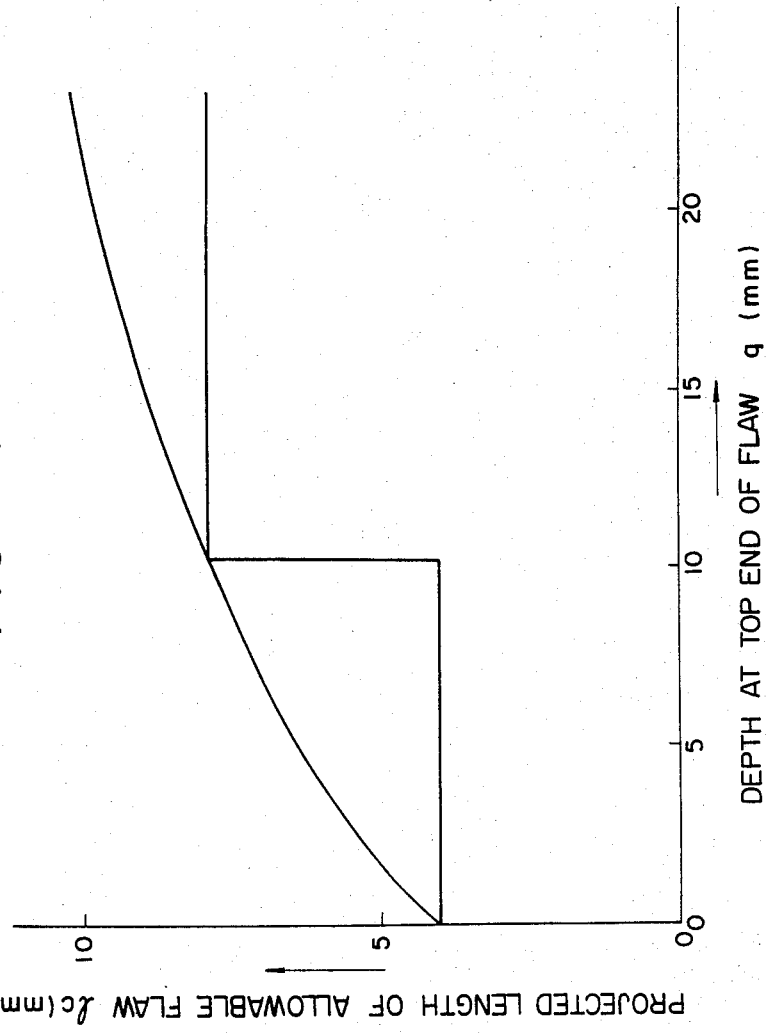
FIG. 17 is a diagram of the depth at the top end of a defect vs. the projected length of allowable flaw.

Now, the invention is described by way of an embodiment applied to the flaw detection of a cast marine propeller 57. In this case, the inspection area for the propeller 57 is 1200×800 mm/blade as indicated by a hatched area in FIG. 15 and the depth of inspection from the blade surface is 20 mm. Among the cavern defects which may exist in the inspection area 58, only harmful defects are selectively displayed on the CRT. The degree of harmfulness is judged by the length $l_c$ as projected in the circumferential direction in consideration of the direction in which the stress is applied. Besides, the degree of harmfulness varies depending upon the depth q at the top end of the defect 3. Therefore, the harmfulness of the defect 3 is defined by the projected length of the defect shown in FIGS. 16(A) and 16(B) and the depth q at the top end of the defect 3 shown in FIG. 17. Consequently, the computer 50 performs the following operations in the final processing stage.

(1) Calculation of the projected defect length:

$$lc = l \cdot \cos \eta \times \sin \alpha \tag{10}$$

in which l is the actual length of the defect, $\eta$ is its inclination and $\alpha$ is its direction from a start line in the radial direction.

(2) Calculation of the depth q at the top end:

$$q = \text{Max}[0, (d - \tfrac{1}{2}l \sin \eta)] \tag{11}$$

in which d is the depth at the center of the defect.

(3) Discrimination of harmful defects:

$$0 \leq q < 10 \text{ and } l_0 \geq 4 \text{ mm} \tag{12}$$

$$0 \leq q \leq 20 \text{ and } l_0 \geq 8 \text{ mm} \tag{13}$$

The harmfulness of defects is defined by two steps in terms of allowable projected dimensions of the defect.

Thus, the computer 50 performs the calculations (10) and (11) as shown in the flowchart of FIG. 15, and, if either one of the conditions (12) and (13) is satisfied, displays the estimated figure of the harmful defects on the printer along with their positional data.

Figure 18A:
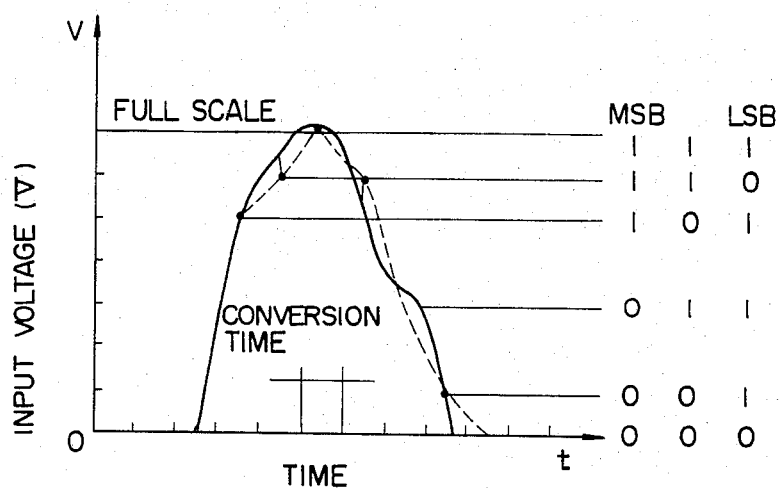
FIGS. 18(A) and 18(B) are diagrammatic illustrations explanatory of the relationship between the input voltage and the number of significant bits.
Figure 18B:
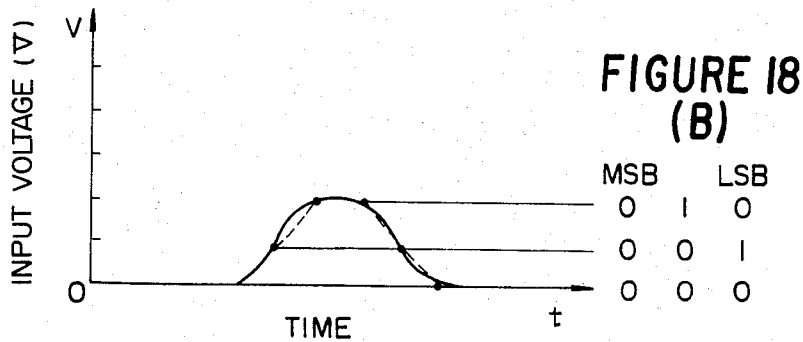

In the digital signal processing as described above, it is the usual practice to use an A/D converter or converters with a vertical resolution of 8–10 bits. As shown in FIG. 18, the vertical resolution is defined by the full scale of the input of the A/D converter. Namely, FIG. 18 shows the relationship between the input voltage of the A/D converter and the number of its effective bits, wherein indicated at (A) is a sufficient input voltage and at (B) an insufficient input voltage, with binary values of 3-bit A/D conversion given on the right side in each case. The points which are connected by broken line are the sampled values before A/D conversion. As clear from FIGS. 1(A) and 1(B), the number of effective bits is 3 when the input has a sufficient voltage but it becomes 2 or less when the voltage of the input is insufficient, resulting in a correspondingly lowered resolution. Therefore, in order to make the most effective use of the resolution of the A/D converter, it is necessary to apply an input voltage which is close to the full scale and, in actual circuits, an amplifier is often inserted in a stage anterior to the A/D converter thereby to adjust the input signal to a level which will ensure the maximum resolution. However, in most cases of nondestructive testing the voltage of the input signal is not known beforehand, so that the adjustment by an amplifier often lead to troubles such as reductions in the resolution of small signals and overscale of large signals. In order to overcome these troubles, the A/D converter should have a high resolution even with regard to input signals of small amplitudes. However, difficulties are often encountered in improving the resolution of the A/D converter due to the limitations which are imposed on the signal processing circuits of subsequent stages.

Figure 20:
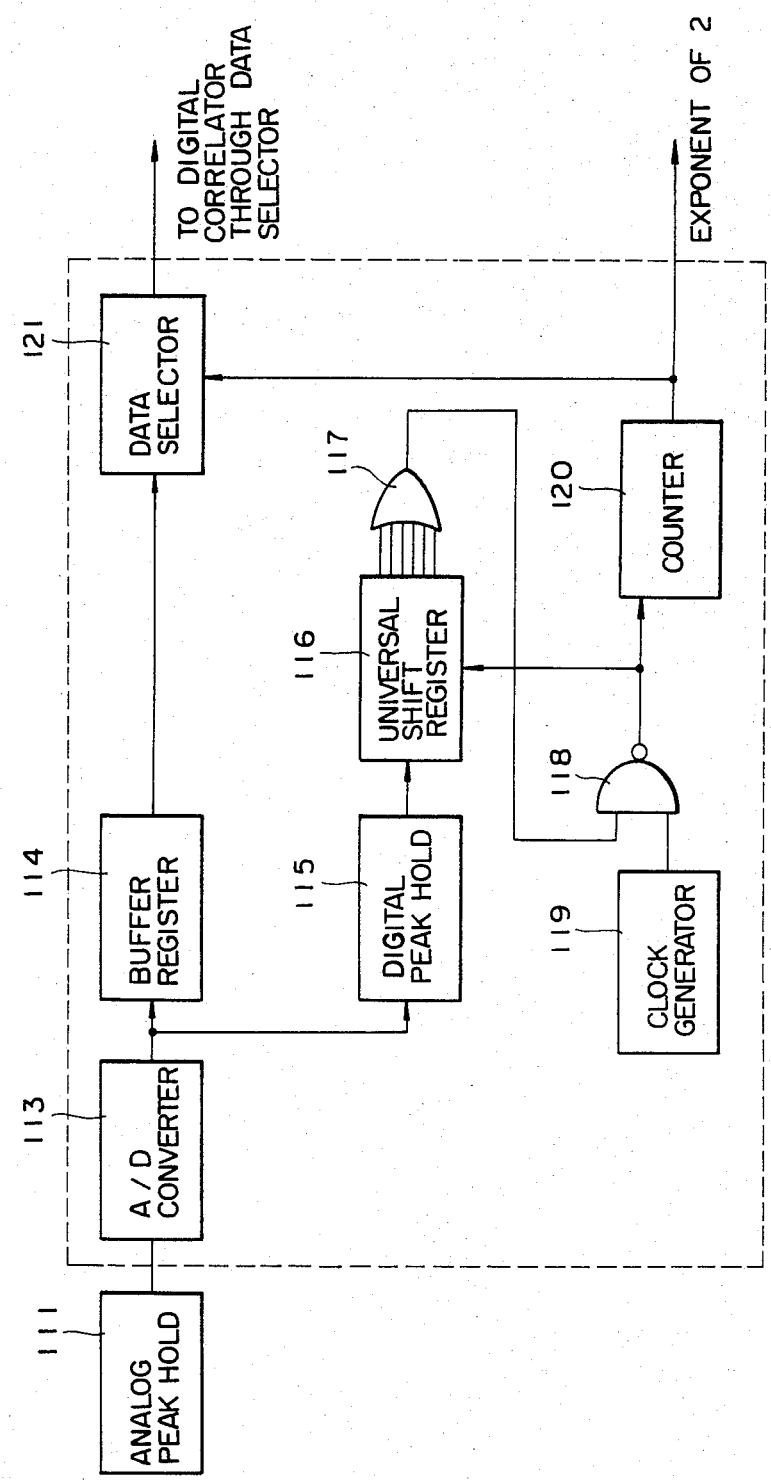
FIG. 20 is a block diagram of a pre-processing circuit.

FIG. 20 illustrates a pre-processing circuit which may be employed in the circuit of FIG. 8 to overcome the above-mentioned limitations and adapted to operate according to the following principles.

Figure 19:
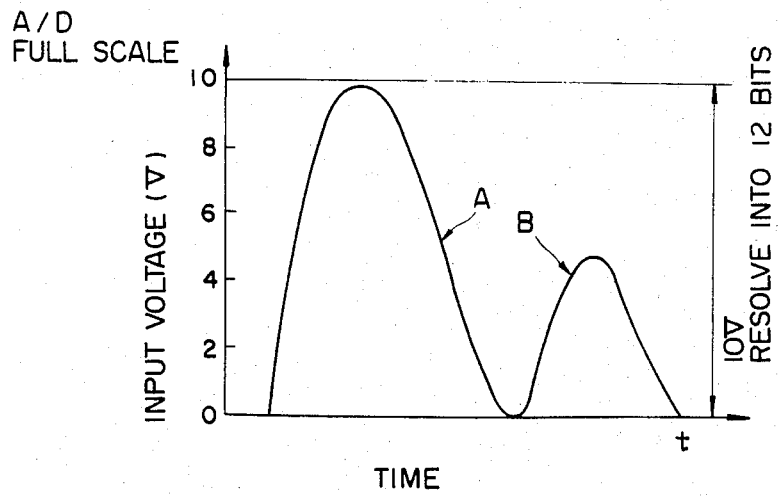
FIG. 19 is a diagrammatic illustration explanatory of the resolution of an A/D converter.

(1) The A/D conversion is executed at a high resolution of, for example, 12 bits for ensuring a sufficient resolution even to input signals of small amplitudes. Consequently, in a case where a full-scale input of 10 V is resolved by 12 bits as shown in FIG. 19, the A/D converter can have a resolution of about 12 bits with respect to a signal of large amplitude as shown at (a) and at the same time a resolution of about 11 bits with respect to a signal of small amplitude as shown at (b).

(2) If the resolution of a signal processing circuit which is located in a posterior stage is 6 bits, for example, the 12-bit signal x cannot be transferred as it is to the posterior stage so that it is decomposed into the form of $x = y \times 2^N$ in which x and y are binary numbers of $x < 2^{12}$ and $y < 2^6$, respectively, and N is 0 or an integer of or smaller than 6.

(3) The value of y is transferred to the signal processing circuit in the posterior stage. In this particular example, the signal processing is linear calculation (calculations involved in digital signal processing are often linear calculations), obtaining the final results by multiplying the results of the above-mentioned calculation by $2^N$.

If the signal of 10 V is directly resolved into 6 bits in this sort of signal processing, the resolution of a signal smaller than 1 V is $64 (= 2^6) \times 1/10 = 6.4 = 2^3$ and thus smaller than 3 bits. However, according to the above-described method, the same small signal is converted into $4096 (= 2^{12}) \times 1/10 = 40.96 < 2^6$ so that, regarding $N = 0$, it can be expressed directly by a binary number of up to 6 bits, retaining a resolution greater than 5 bits.

Figure 21:
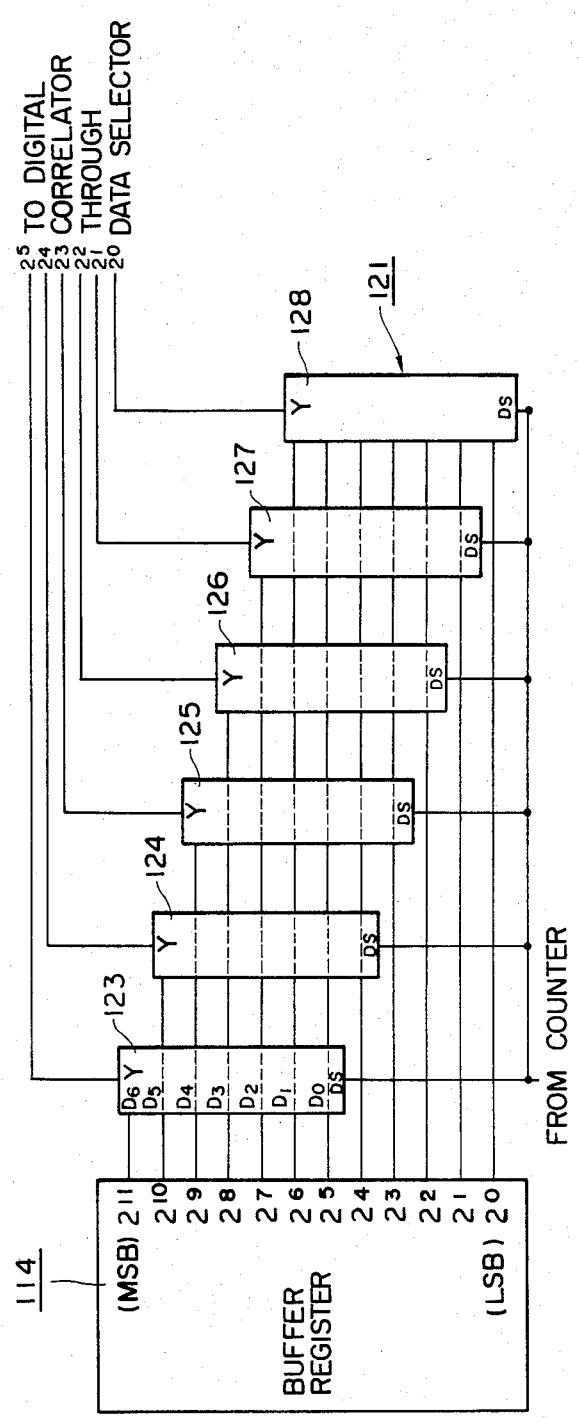
FIG. 21 is a block diagram of a data selector.

Referring to FIG. 20, the pre-processing circuit 112 includes A/D converter 113 (corresponding to the A/D converter 33 to 36 of FIG. 8), buffer register 114, digital peak hold circuit 115, universal shift register 116, OR gate 117, NAND gate 118, clock generator 119, counter 120 and data selector 121 (corresponding to the data selector 42 in FIG. 8). The peak hold circuit 111 corresponds to the peak holding circuit 29 of FIG. 8. The A/D converter 113 of the pre-processing circuit 112 has a 12-bit resolution althrough a correlator 122 in the posterior stage is of 6 bits. The maximum values of the input analog signals are converted into digital quantities with a high resolution of 12 bits to form a detected flaw pattern, transferring the detected flaw pattern to a succeeding stage separately in the form of significant digits of up to $2^6$ and an exponent of 2. More specifically, the detected flaw pattern is temporarily stored in the buffer register 114 of 12 bits × 128, and the maximum value of the transferred detected flaw pattern which consists of 128 points is held in the digital peak hold circuit 115. After the detected flaw pattern is completely stored in the register 114, the maximum value is transferred to the universal shift register 116 which can shift the data to the right and left and up and down. The universal shift register 116 operates in the right-shift mode when it receives the maximum value and then switched to the down-shift mode. In responds to clock pulses from the clock generator 119, a down-shift is repeated until the data is no longer in the upper 6 bits of the universal shift register 116 while confirming the existence of the data in the upper 6 bits of the register by the OR gate 117 and NAND gate 118. At this time, the number of down-shifts is counted by the counter 210. The output value of the counter 120 is fed to address pins of the data selector 121, according to which 6 bits are selected from 12-bit output pins of the buffer register 114 by the data selectors 121 so that the significant digits of the maximum value of the detected flaw pattern in the buffer register 114 are expressed by 6 bits or a smaller number of bits. As shown in FIG. 21, the data selector 121 is constituted by six selectors 123 to 128, the input port of which are connected to the output pins of the buffer register 114 in the positions which are sequentially shifted by one bit. The compressed data of the detected flaw pattern which is selected by the data selector 121 is transferred to the correlator 42 for correlation processing as described hereinbefore. At this time, the significant digits are smaller than 6 bits when the data in the buffer register 114 are smaller than 6 bits.

Thus, the above described pre-processing circuit 112 permits the execution the A/D conversion with a high resolution and to transfer the input signal by the maximum number of digits conforming with the resolution of the digital correlator 42 in the subsequent stage. Accordingly, the data of up to 12 bits in the buffer register 114, for example, the data of $x(\alpha) < 2^{12} (\alpha = 1, 2, 3, \ldots 128)$ are converted into and transferred to the digital correlator 42 in the form of $y(\alpha) \times 2^N (y(\alpha) < 2^6, \alpha = 1, 2, 3, \ldots 128)$, so that the detected flaw patterns with small amplitudes can be treated substantially with the same accuracy as the flaw patterns with large amplitudes.

Figure 22:
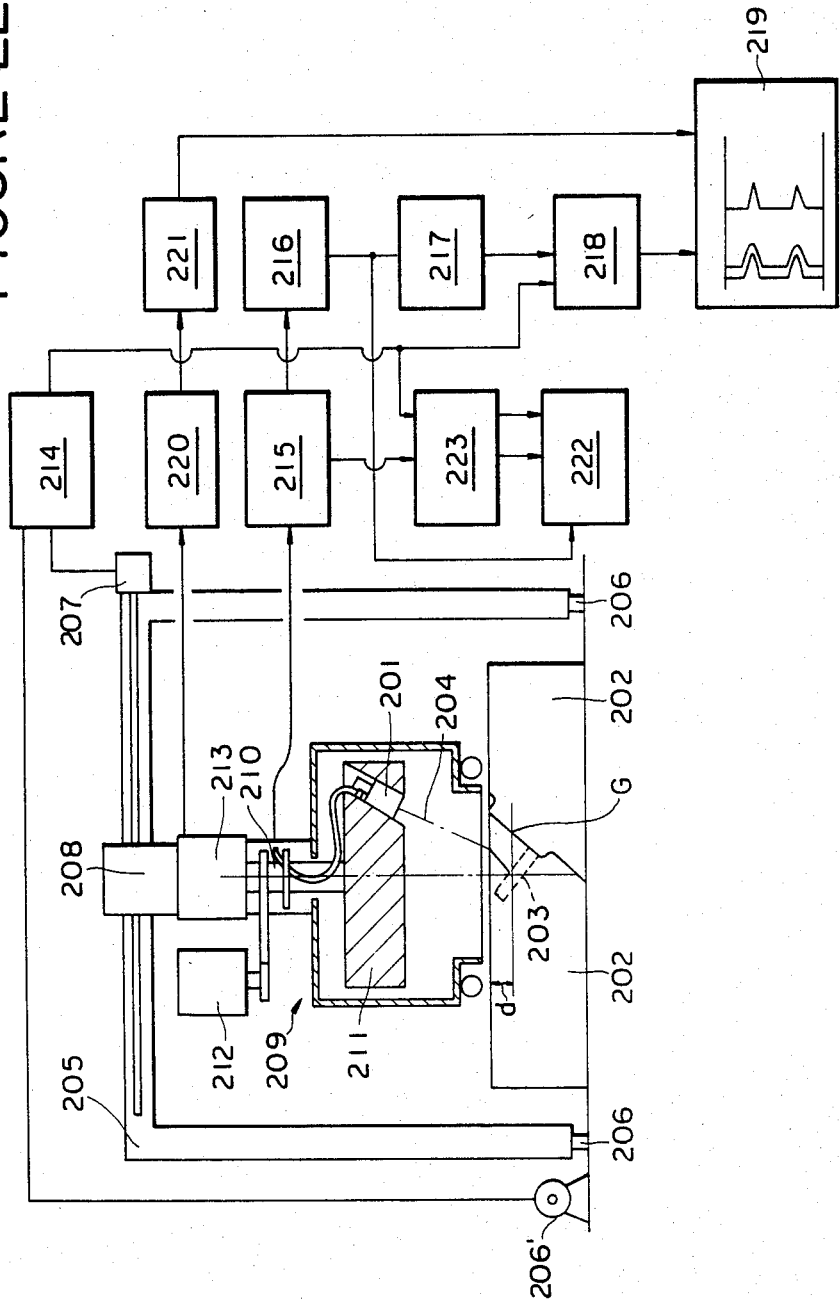
FIG. 22 is a diagrammatic view of a flaw detector of a modified construction.

Referring to FIG. 22, there is shown a modification of the ultrasonic flaw detector according to the invention, wherein the scan mechanism is constituted by a carriage frame 205 which is driven from a motor 206' and movable back and fotth (in the Y-direction) along rails 206 fixed on the opposite sides of an inspecting material 202, and a movable frame 208 which is driven from a motor 207 and movable in the transverse direction (in the X-direction) along a transverse rail of the carriage frame 205. Indicated at 209 is a probe rotating mechanism which includes a rotary block 211 fixedly mounted at the lower end of a vertical rotational shaft 210, mounting thereon a skew probe member 201 to transmit an ultrasonic pulse 204 into the inspecting material 202 in a direction intersecting with the axis of rotation of the rotational shaft 210. The rotational shaft 210 is driven from a motor 212 and coupled with a rotary encoder 213 which detects the rotational angle (or the direction of incidence) of the probe. The probe rotating mechanism 209 is mounted on the movable plate 208. Designated at 214 is a scan controller which control the movements of the carriage frame 205 and the movable frame 208 to scan the probe 201 in the X- and Y-directions. Further, in FIG. 22, indicated at 215 is an ultrasonic flaw detector, at 216 an analog gate, at 217 a peak holding circuit, at 218 an adder, at 219 an X-Y recorder, at 220 a counter, at 221 a D/A converter, at 222 a storage scope, and 223 and adder.

In operation, the carriage frame 205 and movable frame 208 are respectively driven to put the probe 201 in a zig-zag or meandering scan motion, while rotating the same about the axis of rotational shaft 210, and while the transmitting and the ultrasonic beam 204 into the inspecting material 202 along the locus of incident points of the beam. The echoes from a defect 203 which are received by the probe 201 are fed to the analog gate 216 through the flaw detector 215 to pick up the signals in the vicinity of the depth d. The peak value of the signals thus obtained is detected by the peak holding circuit 217, and to this signal the position signal of the scan mechanism is added to the adder 218 as an offset and fed to the X-axis of the X-Y recorder 219. On the other hand, the output pulses of the rotary encoder 213 which are counted by the counter 220 are converted through the D/A converter and fed to the Y-axis and the X-Y recorder 219 as a direction of incidence.

Generally, the reflecting surface O shown in FIG. 1 of a cavern void does not coincide with the intersecting point of the central line of an ultrasonic beam and the rotation axis of a probe.

Therefore, these must coincide in order to obtain an accurate detected flaw pattern.

Figure 24:
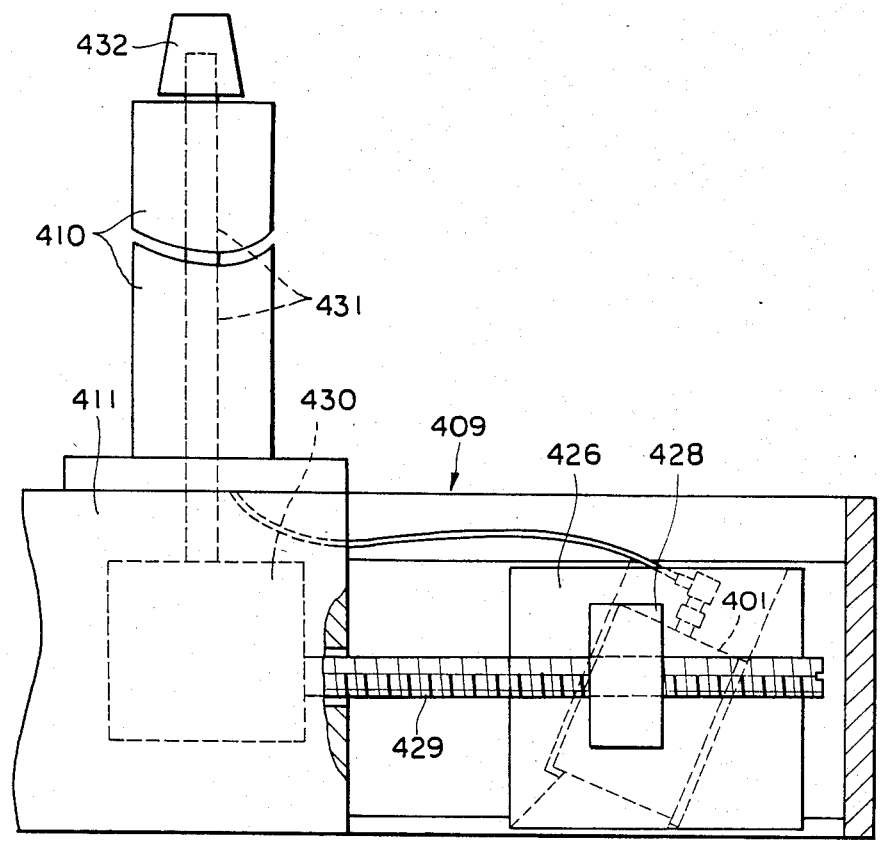
FIG. 24 is a partial cross sectional view of a rotational drive mechanism of a single probe according to one aspect of the present invention.

As can be seen from FIG. 24, a rotational drive mechanism of a single probe enables to vary the rotational radius of the probe. In this FIGURE, a knob 432 is provided for adjusting the rotational radius, 431 represents a transmission rod, 430 represents a gear box, 429 represents a ball screw and 428 represents a ball casing.

Thus, an accurate detected flaw pattern can be obtained by repeating detection with varying the rotational radius and the rotational central axis of a probe above a cavern void. As a result, a detected flaw pattern is indicated on the recording paper of the X-Y recorder 219, obtaining therefrom the direction, inclination and size of the defect 203. The adder 223 produces the X- and Y-axes signals for the storage scope 222 from the sweep signal (of sawtooth wave) of the flaw detector 215, and adapted to adjust the amplitude of the X- and Y-axes signals suitably so that the sweep line of the storage scope will be corresponding to the refraction angle of the ultrasonic beam. Further, the position signal of the scan mechanism is added to the X-axis signal of the storage scope as an offset, and the storage scope displays the so-called B-scope image on the basis of these X- and Y-signals and the Z-axis signal from the analog gate 216. From these data we can estimate the harmfulness, the shape and the position of the detected flaw manually using the equations (2), (3), (4) and (5), and the relations shown by FIGS. 12, 17.

Figure 23:
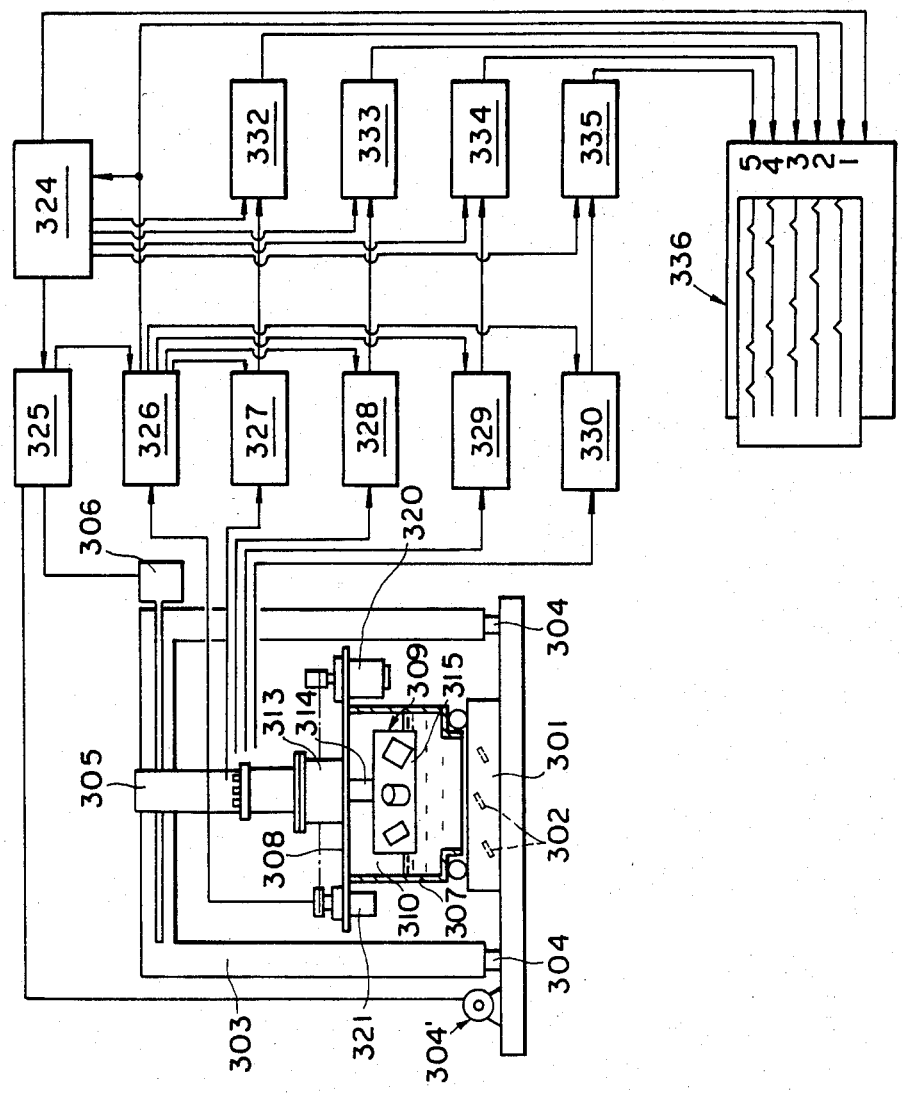
FIG. 23 is a view similar to FIG. 22 but showing another modification of the flaw detector according to the invention.

Referring to FIG. 23, there is shown another modification, similarly employing a carriage frame 303 which is driven from a motor 304 and movable back and forth (in Y-axis direction) along rails 304 fixed on the opposite sides of an inspecting material 302 with a cavern internal defect, and a movable frame 305 which is supported on the carriage frame 403 and movable in the transverse direction (X-axis direction). Denoted at 307 is a tank which accommodates a probe rotating mechanism 309 and receives a supply of a liquid medium 310 in the same manner as in the first embodiment. The probe rotating mechanism 309 has a cylindrical rotational shaft 314 which is rotatably supported in a bearing case 313 on a support plate 308, and a probe holder 315 which is fixedly mounted at the lower end of the rotational shaft 314 and has four inclined probes 316 to 319 built therein at intervals of 90° in the circumferential direction. The probes 316 to 319 have a refraction angle $\theta$ of, for example, 45° and are calibrated to project ultrasonic beams 316a to 319a of 9.2 mm in diameter, respectively. The probes 316 to 319 are located at different distances from the center of rotation so that the ultrasonic beams 316a to 319a intersect the axis of rotation at the depths of 2.5 mm, 7.5 mm, 12.5 mm and 17.5 mm, respectively. Indicated at 320 is a motor for driving the rotational shaft 314 and at 321 a rotary encoder which detects the rotational angle of the probe rotating mechanism 309, which are mounted on the support plate 308 and coupled with the rotational shaft 314 through belt driving mechanisms 322 and 323, respectively. Designated at 324 is a system controller which consists of a microcomputer, at 325 a scan control which controls the movements of the probe rotating mechanism 309 in the X- and Y-axes direction, at 326 a pulse counter, at 327 to 330 pulser receivers which are provided for the respective channels and connected to the corresponding probes 316 to 319 through a slip ring 331, at 332 to 335 analog peak hold circuits, and at 336 a multi-pen recorder.

Similarly to the foregoing embodiments, for the detection of the defect 302 in the material 301, the probe holder 315 of the probe mechanism 309 is rotated about the rotational shaft 314 and at the same time moved in the X- and Y-axis directions to scan the surface of the material 301, transmitting ultrasonic pulses 16a to 19a from the probes 316 to 319 and picking up the echoes from the defect 302 by the respective channels in the same manner as described hereinbefore.

As clear from the foregoing description, the present invention employs a plural number of probes of different depths of inspection on a rotary mechanism to transmit and receive ultrasonic pulses through a corresponding number of channels, forming a detected flaw pattern from the peak value of the echoes received at the flaw detection gate of each channel.

By this way, the following formulae is adopted to estimate the means depth of a flaw;

$$d = \frac{\sum_{i=1}^{4} Smi \cdot di}{\sum_{i=1}^{4} Smi} \quad (14)$$

in which Smi is a maximum value of a detected flaw pattern fo each channel.

Further, the following formulae is used to compensate the received sound pressure drop due to the deviation of central line of an ultrasonic beam from the reflecting surface of a flaw;

$$S'mi = \frac{Smi}{1 - k'|d - di|} \quad (15)$$

in which k' proportional constant depending upon the probe.

Thus, flaw size can be estimated by referring to a Distance-Amplitude curves and S'mi value.

However, the inclination and the direction of a flaw are estimated by using equations (1) through (5).

According to the method of the invention, the efficiency of the flaw detection can be improved to a considerable degree since there is no necessity for repeating inspection of one and same portion for several times at varied depths as in the conventional flaw detection by a single probe. Besides, the harmfulness of a detected defect is judged on the basis of the direction, inclination, size and depth of the defect which are decipherable from its correlations with reference patterns, so that the judgement can be made easily and at a high speed by the use of a computer or hard-wired logic circuits, as compared with the judgement from the detected flaw pattern itself. Moreover, the resolution of input signals can be improved remarkably by the provision of the preprocessing circuit which employs a A/D converter of high resolution and which is adapted to transfer the converted digital signals by a bit number conforming with the resolution of the correlator of the subsequent stage.

What is claimed is:

1. An ultrasonic flaw detection method for detecting internal defects of a material, said method comprising the steps of:

providing on a rotary body a plural number of inclined probes in equidistant positions in the circumferential direction of said rotary body to provide a corresponding number of channels to transmit and receive ultrasonic pulses in a direction intersecting the axis of rotation of said rotary body at different depths in an inspection zone within a material which is positioned opposite to said probes wherein a flaw, if one exists, in said material reflects said transmitted pulses from said probes to provide said received pulses back to said probes;

turning said rotary body to revolve said probes through 360° about said axis of rotation while transmitting and receiving the ultrasonic pulses;

producing a plural number of detected flaw patterns in relation with the respective directions of incidence of said ultrasonic beams, from the peak values of the echoes received at the detection gates of the respective channels; and deciphering the direction, inclination, size and depth of a detected defect from correlation processing of said detected flaw patterns with a number of predetermined reference patterns for judging the harmfulness of the detected defect.

2. An apparatus of ultrasonic flaw detection for recognizing internal cavern defects of a material, said apparatus comprising:

a plural number of probes mounted on a rotary body in equidistant positions in the circumferential direction of said rotary body for providing a plural number of channels for transmitting and receiving the ultrasonic pulses transmitted in a direction intersecting the axis of rotation of said rotary body at different depths of an inspection range within a material which is positioned opposite to said probes wherein a flaw, if one exists, in said material reflects said transmitted pulses from said probes to provide said received pulses back to said probes;

drive means for turning said rotary body to revolve said probes through 360° about said axis of rotation while transmitting and receiving said ultrasonic pulses;

peak-holding and memory means provided for each one of said channels for producing and storing a plural number of detected flaw patterns in relation with the directions of incidence of said ultrasonic pulses from the peak values of echoes received at flaw detecting gates of the respective channels;

correlator for diciphering the direction, inclination, size and depth of said detected defect by correlation processing of said detected flaw patterns with a number of predetermined reference patterns; and means for judging the harmfulness of the detected defect according to the results of said correlation processing.

3. An apparatus as set forth in claim 2, wherein said rotary body is supported on a scan mechanism movable in the transverse and longitudinal directions of a material to be inspected for scanning the said probes in a meandering fashion along the opposing side of said material.

4. An apparatus as set forth in claim 2, wherein said rotary body is a probe holder fixedly mounted at the lower end of a vertical rotational shaft and accommodated in a water tank with the distal ends of said probes immersed in water in said tank.

5. An apparatus as set forth in claim 2, wherein said detection gate of each channel is connected to said correlator through an input circuit including a pluser receiver, an analog peak hold circuit, an A/D converter, a shift register and a data selector.

6. A method of ultrasonic flaw detection suitable for detecting internal defects of a material, said method comprising the steps of:
providing a probe on a rotary body to transmit and receive ultrasonic pulses in a direction intersecting the axis of rotation of said rotary body in an inspecting zone of a material which is positioned opposite to said probe wherein a flaw, if one exists, in said material reflects said transmitted pulses from said probe to provide said received pulses back to said probe;
turning said rotary body to revolve said probe through 360° about said axis of rotation while transmitting and receiving said ultrasonic pulses;
indicating on a display medium the peak values of echoes received at a detection gate as a detected flaw pattern in relation with the direction of incidence of said ultrasonic pulses; and
judging the direction, inclination and size of a defect from said detected flaw pattern.

7. A method of ultrasonic flaw detection suitable for detecting internal defects of a material, said method comprising the steps of:
providing a probe on a rotary body to transmit and receive ultrasonic pulses in a direction intersecting the axis of rotation of said rotary body in an inspection zone of a material which is positioned opposite to said probe wherein a flaw, if one exists, in said material reflects said transmitted pulses from said probe to provide said received pulses back to said probe;
turning said rotary body to revolve said probe through 360° about said axis of rotation while transmitting and receiving said ultrasonic pulses;
moving said probe in the radial direction of said rotary body at a position where an echo is received at a detection gate to find a point where said echo shows a peak value;
revolving said probe again at said point and indicating on a display medium the peak values of said echoes as a detected flaw pattern in relation with the direction of incidence of said ultrasonic beam; and
judging the direction, inclination, size and depth of a defect from said detected flaw pattern.

8. A method of ultrasonic flaw detection suitable for detecting internal defects of a material, said method comprising the steps of:
providing on a rotary body a plural number of probes at equidistant positions in the circumferential direction of said rotary body to provide a plural number of channels for transmitting and receiving the ultrasonic pulses in a direction intersecting the axis of rotation of said rotary body at different depths in an inspection zone of said material which is positioned opposite to said probes wherein a flaw, if one exists, in said material reflects said transmitted pulses from said probes to provide said received pulses back to said probes;
turning said rotary doby to revolve said proves through 360° about said axis of rotation while transmitting and receiving said ultrasonic pulses;
indicating on a recording medium the peak values of echoes received at the detection gates of the respective channels as detected flaw patterns in relation with the direction of incidence of the ultrasonic beam of the corresponding channel; and
judging the direction, inclination, size and depth of a defect from said detected flaw patterns of the respective channels.

* * * * *